(12) United States Patent
Kantor et al.

(10) Patent No.: US 7,175,345 B2
(45) Date of Patent: *Feb. 13, 2007

(54) DENTAL X-RAY APPARATUS

(75) Inventors: Arkady Kantor, Buffalo Grove, IL (US); Roberto Molteni, Arlington Heights, IL (US); Daniel P. Murphy, York, PA (US); Todd R. Carlson, Glenview, IL (US)

(73) Assignee: Gendex Corporation, Washington, DC (US)

( * ) Notice: Subject to any disclaimer, the term of this patent is extended or adjusted under 35 U.S.C. 154(b) by 375 days.

This patent is subject to a terminal disclaimer.

(21) Appl. No.: 10/779,366

(22) Filed: Feb. 13, 2004

(65) Prior Publication Data
US 2006/0078090 A1  Apr. 13, 2006

Related U.S. Application Data

(60) Continuation of application No. 10/279,607, filed on Oct. 24, 2002, now abandoned, which is a division of application No. 09/577,443, filed on May 24, 2000, now abandoned.

(60) Provisional application No. 60/135,856, filed on May 25, 1999.

(51) Int. Cl.
*H05G 1/02* (2006.01)
(52) U.S. Cl. ..................................... 378/197
(58) Field of Classification Search .............. 378/38, 378/39, 40, 121, 193, 197, 203
See application file for complete search history.

(56) References Cited

U.S. PATENT DOCUMENTS

| 2,946,892 | A |   | 7/1960  | Bas-Taymaz ............ 378/113 |
| 3,125,679 | A |   | 3/1964  | Ohde et al. ............. 378/102 |
| 3,934,164 | A |   | 1/1976  | Braun et al. ............ 378/125 |
| 4,104,530 | A |   | 8/1978  | Weiss ..................... 378/38 |
| 4,104,531 | A |   | 8/1978  | Weiss ..................... 378/38 |
| 4,104,532 | A |   | 8/1978  | Weiss ..................... 378/38 |
| 4,157,476 | A | * | 6/1979  | O'Connor ............... 378/203 |
| 4,167,670 | A |   | 9/1979  | Ingold .................... 378/105 |
| 4,196,351 | A |   | 4/1980  | Albert ................... 378/98.6 |
| 4,317,040 | A |   | 2/1982  | Wuerflein ............... 378/110 |
| 4,323,779 | A |   | 4/1982  | Albert ................... 378/98.6 |
| 4,346,983 | A |   | 8/1982  | Jeromin et al. ........... 378/28 |
| 4,357,537 | A |   | 11/1982 | Rattner .................. 378/103 |
| 4,612,582 | A |   | 9/1986  | Tucker ................... 348/749 |
| 4,795,654 | A |   | 1/1989  | Teleki ................... 428/635 |
| 4,840,471 | A |   | 6/1989  | Mitani et al. ........... 359/722 |
| 5,077,771 | A |   | 12/1991 | Skillicorn et al. ....... 378/102 |
| 5,111,493 | A |   | 5/1992  | Siedband ................ 378/103 |

(Continued)

FOREIGN PATENT DOCUMENTS

EP  0 106 482  9/1983

(Continued)

*Primary Examiner*—Courtney Thomas
(74) *Attorney, Agent, or Firm*—McNees Wallace & Nurick LLC

(57) ABSTRACT

A dental x-ray apparatus (10) includes a tube head (11) formed from a cast zinc material. Structural components of tube head (11) include such component (20) formed from a plastic material impregnated with a high molecular weight substance, such as barium sulfite. X-ray apparatus 10 has a control panel (15) in close proximity to the tube head (11), and is preferably DC powered.

13 Claims, 3 Drawing Sheets

U.S. PATENT DOCUMENTS

| | | | |
|---|---|---|---|
| 5,153,900 A | 10/1992 | Nomikos et al. | 378/65 |
| 5,384,820 A | 1/1995 | Burke | 378/135 |
| 5,434,418 A | 7/1995 | Schick | 250/370.11 |
| 5,454,022 A | 9/1995 | Lee et al. | 378/98.8 |
| 5,458,111 A | 10/1995 | Coin | 600/560 |
| 5,557,650 A | 9/1996 | Guida et al. | 378/154 |
| 5,631,943 A | 5/1997 | Miles | 378/102 |
| 5,912,942 A | 6/1999 | Schick et al. | 378/98.8 |
| 6,044,131 A | 3/2000 | McEvoy et al. | 378/162 |
| 6,295,337 B1 | 9/2001 | Thevenin et al. | 378/117 |
| 6,644,853 B1 | 11/2003 | Kantor et al. | 378/203 |
| 6,945,694 B2 * | 9/2005 | Kantor et al. | 378/203 |

FOREIGN PATENT DOCUMENTS

| | | |
|---|---|---|
| EP | 0 141 985 | 9/1984 |
| EP | 0 544 974 | 6/1993 |
| EP | 0 869 534 | 1/1995 |
| EP | 0 666 483 | 8/1995 |
| JP | 10188865 A | 7/1995 |
| WO | WO 92/04727 | 3/1992 |
| WO | WO 95/09520 | 4/1995 |

* cited by examiner

DENTAL X-RAY APPARATUS

RELATED APPLICATION

This application is a continuation Application Ser. No. 10/279,607, filed Oct. 24, 2002, now abandoned, which is a divisional of Application Ser. No. 09/577,443, filed May 24, 2000, now abandoned, which claims the benefit of U.S. Provisional Application 60/135,856, filed May 25, 1999.

TECHNICAL FILED

The present invention is generally directed toward a dental x-ray apparatus. More particularly, the invention is directed toward an x-ray apparatus having a tube head formulated from a cast zinc material. Further, the invention also provides tube head components fabricated from a high molecular weight material, such as barium sulfite. More specifically, the tube head components are fabricated from a barium sulfite-charged plastic material. Further, the present invention is directed toward a DC powered x-ray dental apparatus.

BACKGROUND OF THE INVENTION

X-ray generators of small or moderate power for medical radiological application, normally use a fixed-anode x-ray tube (verses a rotating-anode x-ray tube as used when large power is required). In this case, the x-ray tube is usually contained in the same oil-filled housing as the high-voltage transformer and other components of the high-voltage circuit, and such an assembly is called a tubehead. During the last several years, x-ray generators commercially available for dental application (whether intraoral, panoramic, or other) have adopted this general design almost universally.

Inside the tubehead, the x-ray tube is supported by a mechanical part known as the tube holder, made out of a high-insulate and high electric tensile strength material, which performs essentially two functions:

1) to securely and precisely hold the x-ray tube in position, in relation to the surrounding construction and in particular to the output windows and the external Beam-Limiting-Device; it ensures the accurate geometrical position of the x-ray source;

2) to generate high-voltage insulation between the x-ray tube (one or more of whose electrodes are at extremely high electrical potential) and the surrounding constructive metallic parts (in particular the housing) which are grounded.

In order to provide near-focus shielding against radiation from the x-ray tube (primary and extrafocal) in all directions except through a suitable output windows (thus greatly reducing the additional radiation shielding required for the housing as a whole), the tube holder is usually surrounded by a lead jacket, at least at the anode side and except for a small opening in correspondence with the wanted x-ray beam path.

The design and construction of this lead jacket may be critical, as any sharp or pointed detail (e.g., such as the thread of a screw) should be avoided because they imply singularities in the electric field and hence may cause high-voltage discharges.

Other structural components of the tube head, such as the housing or other such components, have typically been formulated from steel sheet metal, or cast aluminum alloys. Fabrication with welded steel sheet metal is relatively expensive, and quality might be difficult to control because it depends on the accuracy of the individual manufacturing process. Cast aluminum alloys requires special precautions to prevent oil leakage due to the fact that the material is often porous.

In both cases, but particularly when using aluminum, additional x-ray shielding is necessary. Lead plates or foil normally provide this shielding. Lead is an undesirable material to work with because of environmental and health issue concerns. In addition, lead shielding can either be placed inside the housing or outside the housing. In the case of inside shielding, the efficacy of the shielding cannot be visually inspected over time to check for example, for positioning of the lead plates. Further, the lead and its associated components, such as lead protective paints, are potential contaminants to the dielectric-oil, and potentially can spoil the insulating performance of the oil. When placed outside the housing, the shielding may be mechanically damaged (lead is a soft material) by improper handling during production, installation or service. Further, the harmful lead is exposed. A need exists therefore for a dental x-ray apparatus having improved shielding and structural components.

DISCLOSURE OF THE INVENTION

It is therefore, an object of the present invention to provide a dental x-ray apparatus.

It is another object of the invention to provide a dental x-ray apparatus having improved structural and shielding components.

It is a further object of the invention to provide dental x-ray apparatus having a tube head formed from a cast zinc material.

It is an additional object of the invention to provide a dental x-ray apparatus having a tube head with structural and shielding components formed from a plastic impregnated with a high molecular weight material.

It is still a further object of the present invention to provide a dental x-ray apparatus wherein the structural components are formed from a plastic impregnated with barium sulfite.

In general, a dental x-ray apparatus comprises a housing, an x-ray tube, and structural components to support said x-ray tube. The housing is formulated from a cast of zinc material. The structural components, such as the tube carrier, are formulated from a plastic or resin material impregnated with a high molecular weight radiation absorber. The radiation absorber is preferably barium sulfite. These and other objects of the present invention, which shall become clear from the following description, are accomplished by the invention as hereinafter described.

BRIEF DISCUSSION OF THE DRAWINGS

PREFERRED EMBODIMENTS FOR CARRYING OUT THE INVENTION

Figure 1:
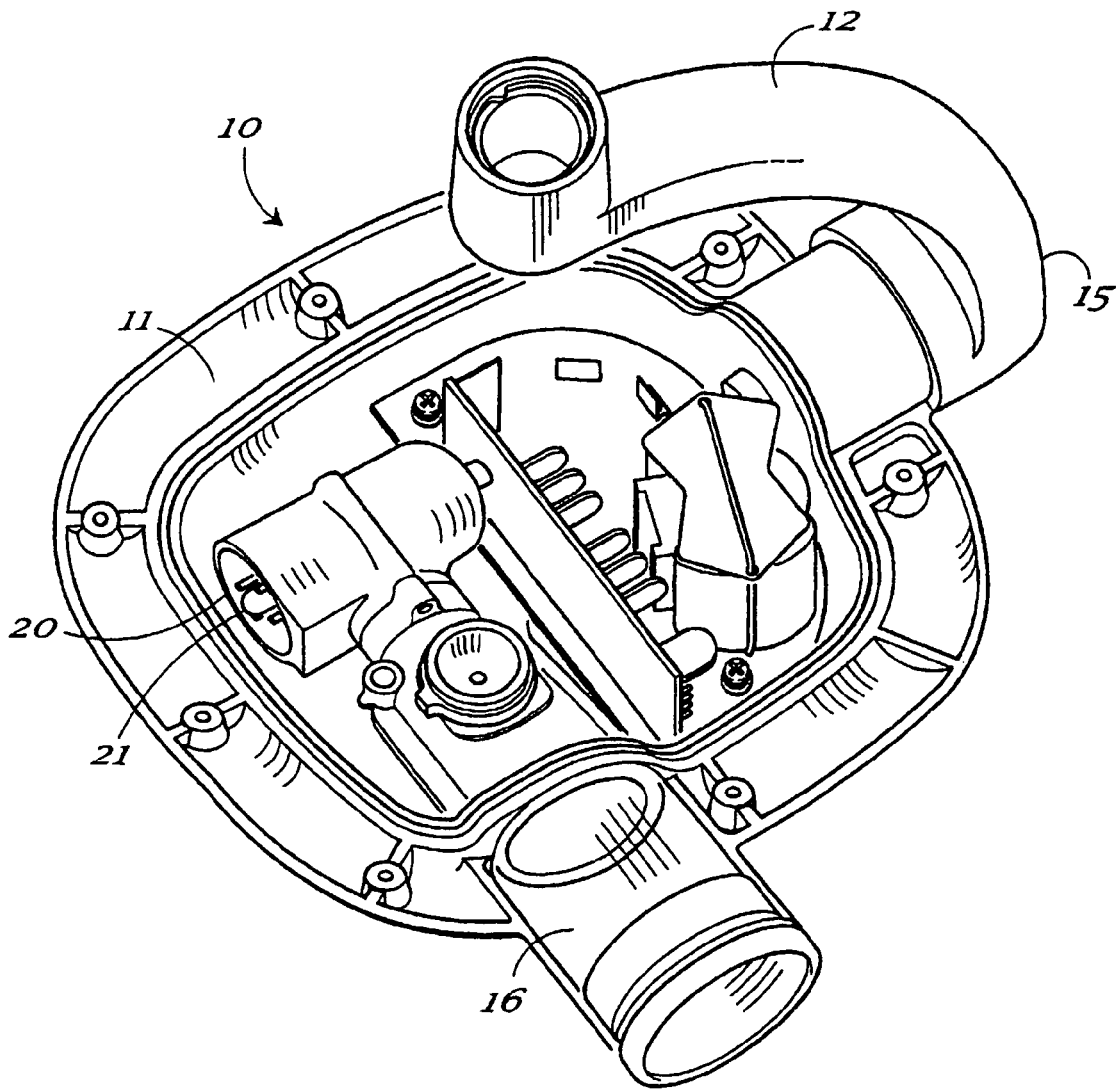
FIG. 1 is a perspective view of a dental x-ray tube head showing the top portion of the main housing removed.

A dental x-ray apparatus according to the concepts of the present invention is shown by way of example by the number 10 on the attached drawings. Dental x-ray apparatus 10 includes a tube head 11 supported on a yoke 12. Yoke 12 is in turn supported by support apparatus 13. A control unit 14 is provided and may also be supported by yoke 12. A unique aspect of the present invention is that control operations may also be preformed by control panel 15 located on yoke 12. It should be understood that control panel 15 may be placed anywhere in proximity to tube head 11, and may even be on tube head 11 itself. Any location for control panel 15 in close proximity tube head 11 is within the scope of the present invention. As is conventional, tube head 11 is provided with collimator 16. The operation of the x-ray apparatus is conventional except as otherwise noted herein. A conventional dental x-ray tube head is shown by way of example in U.S. Pat. No. 4,157,476 which is hereby incorporated by reference for such disclosure.

Tube head housing 11 may be fabricated in any shape or design. An exemplary such tube head is shown by way of example on the accompanying drawings. Tube head 11 is preferably fabricated from a cast of zinc material. Zinc has a sufficiently high atomic number, and hence x-ray attenuation coefficient, as to provide enough shielding to secondary x-rays, i.e. against radiation leakage, without need for additional shielding such as those made from lead. Further, zinc lends itself well to casting, so it is suitable for such parts as a housing for tube head 11 with relatively thin and large walls. As is otherwise conventional, tube head 11 may be used to contain a dielectric oil. Further, zinc has sufficient mechanical properties to make it useful for structural components of the tube head. Zinc is also fairly inexpensive, is compact and has no inherent porosity. An additional advantage of zinc is that it is relatively lightweight.

Figure 2:
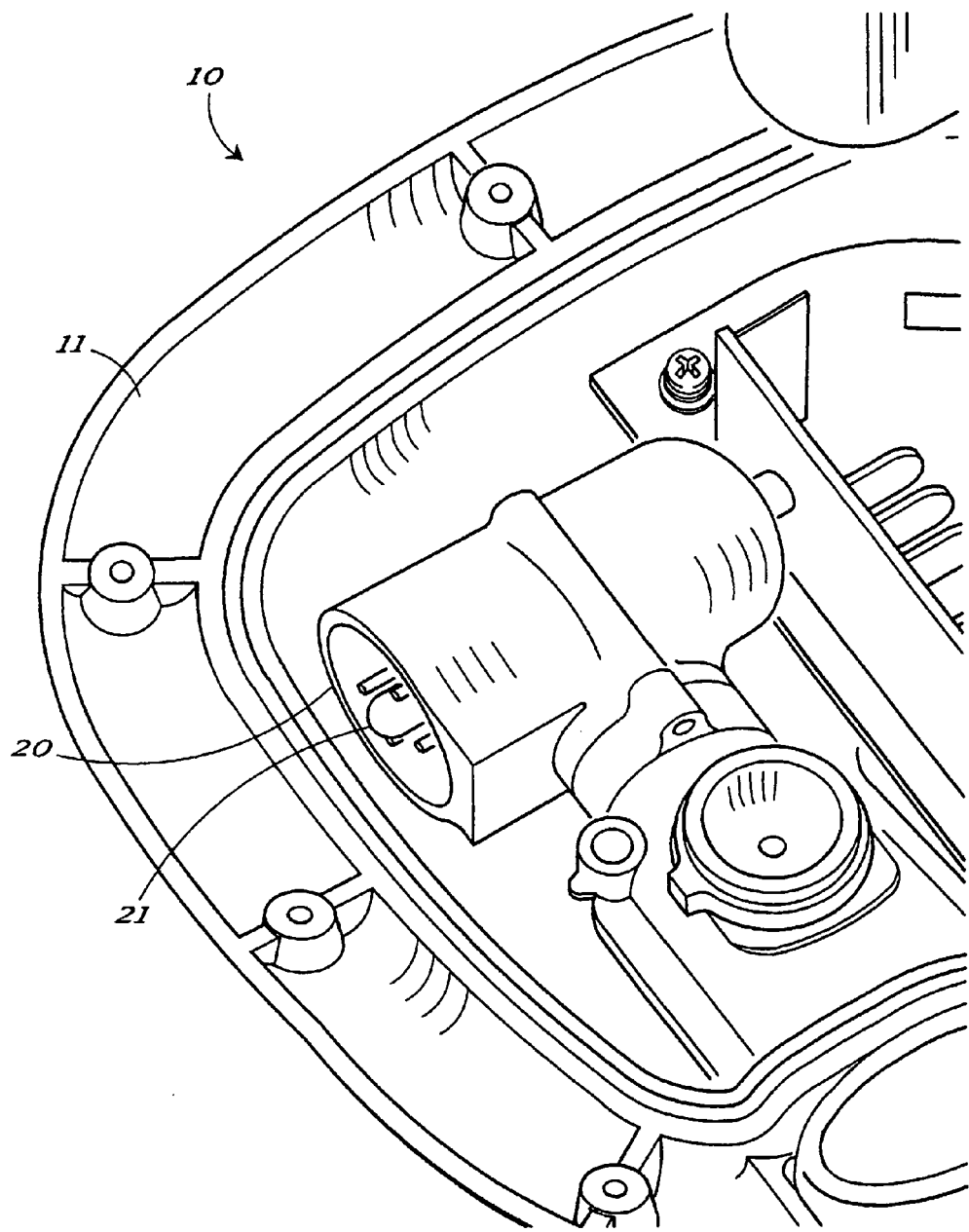
FIG. 2 is a close-up, perspective view of one portion of the tube head of FIG. 1.
Figure 3:
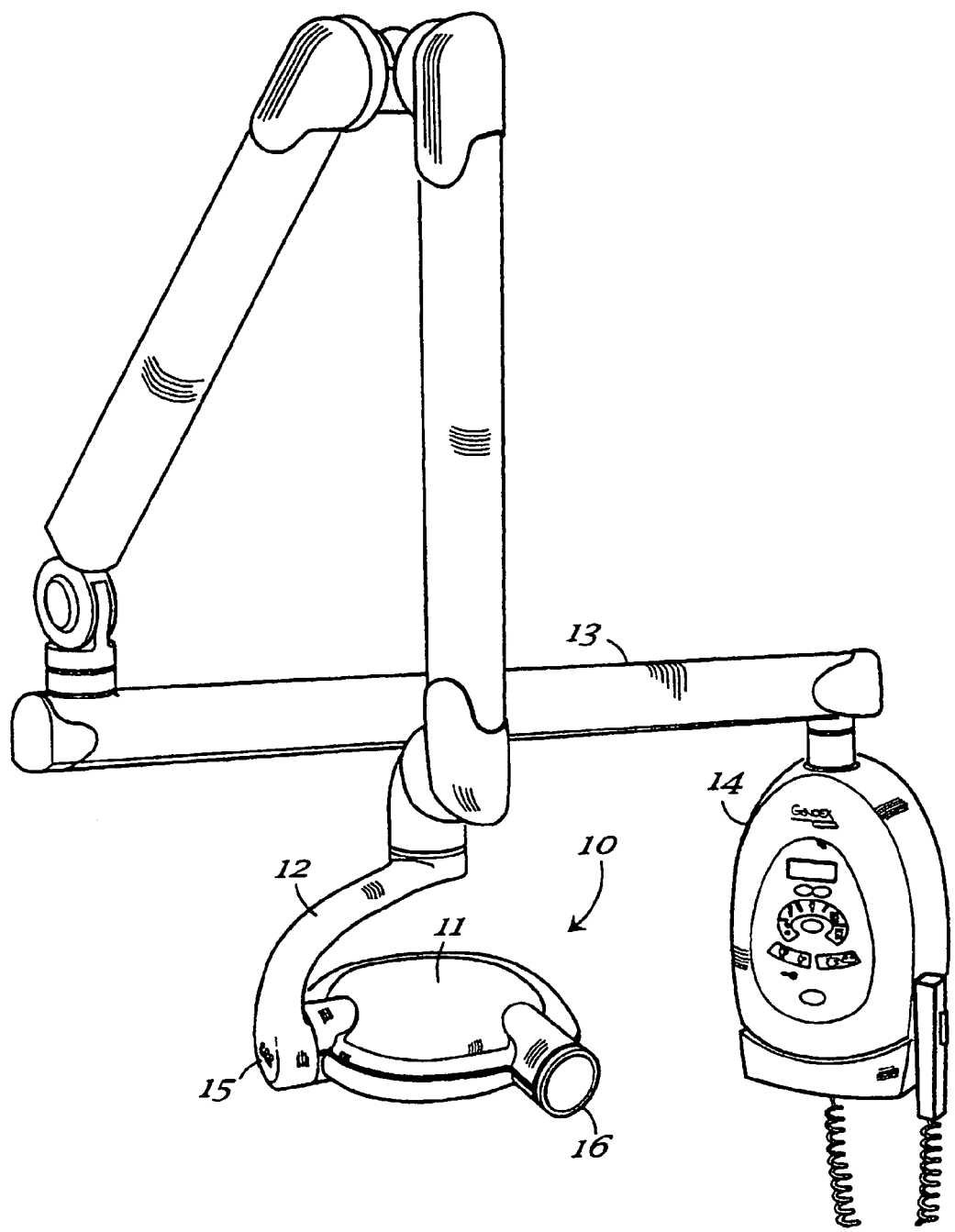
FIG. 3 is a front perspective view of an x-ray apparatus incorporating the concepts of the present invention.

As shown in FIGS. 1 and 2, other components of the tube head 11 such as carrier 20 which is used to support an x-ray tube 21 is preferably fabricated from a plastic material impregnated with a radiation absorber. One preferred radiation absorber is barium sulfite. Barium sulfite is known for use as a contrast medium swallowed by a patient during gastro-intestinal radiography and as an additive to concrete for enhancing the radiation-shielding properties of masonry. It is generally considered to be not hazardous to health. Barium sulfite is also used as a charge added to certain types of products to enhance or change their mechanical properties. In the present invention, barium sulfite is used as an additive to the plastics of constructive parts inside the tube head, such as the tube holder or carrier 20, for the purpose of imparting radiation-shielding properties to otherwise radiation-transparent plastics. By making the x-ray tube holder out of a barium sulfite-charged plastic, the holder 20, which normally has a lead jacket, is free of such additional shielding. It is to appreciated that lead, a generally hazardous and polluting material need not be used. Further, holder 20 is a one part component, thus, eliminating the need for a lead jacket. Further, the potential of a high-voltage dielectric discharge is reduced because of the absence of a metallic conductive part (potentially with sharp edges), in the immediate vicinity of the high voltage tube 21.

Although otherwise conventional, is it preferred that the present x-ray apparatus be powered by a DC power supply.

It should be apparent that the present invention provides a dental x-ray apparatus carrying out the objects of the invention as set forth hereinabove. The invention has been exemplified about an with respect to the attached drawings, without attempting to show all of the variations that will be readily apparent to those skilled in the art. The scope of the invention shall only the determined by the attached claims.

What is claimed is:

1. A dental x-ray apparatus having an x-ray tube disposed within a tubehead and the tubehead being supported by a yoke, the yoke having a control panel to perform control operations.

2. The dental x-ray apparatus of claim 1 wherein the tubehead is formed from cast zinc or zinc alloy.

3. The dental x-ray apparatus of claim 1 wherein the tubehead comprises a plurality of components and at least one of the tubehead components is formed from a plastic material impregnated with a radiation absorber.

4. The dental x-ray apparatus of claim 3 wherein the radiation absorber is a barium compound.

5. The dental x-ray apparatus of claim 4 wherein the barium compound is barium sulfite.

6. The dental x-ray apparatus of claim 5 wherein a tubehead component is an x-ray tube holder.

7. A dental x-ray apparatus comprising:
   a tubehead, the tubehead comprising a housing, a collimator, a x-ray tube, high-voltage circuitry including one or more high-voltage transformers, dielectric oil and a tube holder to support the x-ray tube, wherein the collimator, the x-ray tube, the high voltage circuitry and the tube holder are disposed in the housing and soaked in dielectric oil;
   a yoke connected to the tubehead to support the tubehead;
   a support structure connected to the yoke to support the yoke; and
   a control panel to perform control operations, the control panel being located on one of the yoke and the tubehead.

8. The dental x-ray apparatus of claim 7 wherein the tubehead is formed from cast zinc or zinc alloy.

9. The dental x-ray apparatus of claim 7 wherein the tube holder is formed from a plastic material impregnated with a radiation absorber.

10. The dental x-ray apparatus of claim 9 wherein the radiation absorber is a barium compound.

11. The dental x-ray apparatus of claim 10 wherein the barium compound is barium sulfite.

12. The dental x-ray apparatus of claim 7 wherein the control panel is located on the yoke.

13. The dental x-ray apparatus of claim 7 wherein the control panel is located on the tubehead.

* * * * *

UNITED STATES PATENT AND TRADEMARK OFFICE
CERTIFICATE OF CORRECTION

| | |
|---|---|
| PATENT NO. | : 7,175,345 B2 |
| APPLICATION NO. | : 10/779366 |
| DATED | : February 13, 2007 |
| INVENTOR(S) | : Kantor et al. |

It is certified that error appears in the above-identified patent and that said Letters Patent is hereby corrected as shown below:

On the Title page, Field 56, References Cited, "4,795,654 A  1/1989" should be -- 4,795,654 A  1/1986 --, In column 1, line 1, "continuation Application" should be -- continuation of Application --.

Signed and Sealed this

Twentieth Day of November, 2007

JON W. DUDAS
*Director of the United States Patent and Trademark Office*